United States Patent [19]
Levin et al.

[11] Patent Number: 6,114,551
[45] Date of Patent: Sep. 5, 2000

[54] OLEFIN EPOXIDATION CATALYSTS

[75] Inventors: Doron Levin, Bala Cynwyd, Pa.; Clarence D. Chang, Princeton, N.J.; Shifang Luo, West Chester, Pa.; Jose G. Santiesteban, West Chester, Pa.; James C. Vartuli, West Chester, Pa.

[73] Assignee: Mobil Oil Corporation, Fairfax, Va.

[21] Appl. No.: 09/412,773

[22] Filed: Oct. 4, 1999

[51] Int. Cl.$^7$ ................................................. C07D 305/00
[52] U.S. Cl. ............................................. 549/510; 502/60
[58] Field of Search ............................... 549/510; 502/60

[56] References Cited

U.S. PATENT DOCUMENTS

| | | | |
|---|---|---|---|
| 4,883,260 | 11/1989 | Neri et al. | 549/531 |
| 5,374,747 | 12/1994 | Saxton et al. | 549/531 |
| 5,621,122 | 4/1997 | Saxton et al. | 549/529 |

OTHER PUBLICATIONS

X.Gao, I.E. Wachs, "Titania–Silica as Catalyst: Molecular Structural Characteristics and Physico–Chemical Properties," Catal. Today, 1999, 51, 233–254.

*Primary Examiner*—Amelia Owens

[57] ABSTRACT

A method of synthesizing an olefin epoxidation catalyst comprises the step of treating a porous crystalline aluminosilicate material having an X-ray diffraction pattern including d-spacing maxima at 12.4±0.25, 6.9±0.15, 3.57±0.07 and 3.42±0.07 Angstrom, such as MCM-22, with a dealuminating agent under conditions effective to remove framework aluminium from the material and produce a dealuminated product. The dealuminated product is then treated with a titanium-containing material under conditions effective to insert titanium into the dealuminated product and produce a titanium-containing, dealuminated catalyst composition.

The resultant catalyst is useful in the epoxidation of olefins, such as propylene and cyclohexene, with hydrogen peroxide and organic hydroperoxides.

8 Claims, No Drawings

OLEFIN EPOXIDATION CATALYSTS

FIELD OF THE INVENTION

This invention relates to the synthesis and use of olefin epoxidation catalysts.

BACKGROUND TO THE INVENTION

Olefin epoxidation is an industrially important reaction, especially the epoxidation of propylene to propylene oxide. In 1992, 7.2 billion pounds of propylene oxide were is produced, with 50% being synthesized via propylene epoxidation with t-butylhydroperoxide or ethylbenzene hydroperoxide. The catalysts currently used in these processes are either homogeneous molybdenum compounds or heterogeneous silica-supported titania materials.

Extensive spectroscopy studies of silica-supported titanium oxides have suggested that the active centers in these catalysts are the isolated surface titanium atoms that form the $O=Ti(OSi)_2$ structure with the silica framework rather than bulk $TiO_2$ particles. Bulk $TiO_2$ particles appear to be undesirable in that they catalyze the non-selective decomposition of hydroperoxides (X. Gao, I. E. Wachs, "Titania-Silica as Catalysts: Molecular Structural Characteristics and Physico-Chemical Properties," Catal. Today, 1999, 51, 233–254).

To prevent the formation of bulk $TiO_2$ phases in heterogeneous titanium-silica catalysts, the isomorphous substitution of Si (IV) by Ti (IV) in zeolites has been investigated. These studies resulted in the successful synthesis of a number of titanium silicates, including TS-1, TS-2, Ti-beta, Ti-ZSM-48 and Ti-MCM-41. Spectroscopic studies have confirmed the presence of framework titanium atoms in these silicates and the absence of bulk $TiO_2$ particles. Further investigations have also demonstrated catalytic activities of these titanium silicates in olefin epoxidation. For example, U.S. Pat. No. 4,833,260 discloses the use of TS-1 in the epoxidation of propylene with hydrogen peroxide. In addition, U.S. Pat. Nos. 5,374,747 and 5,621,122 disclose epoxidation of olefins with hydrogen peroxide or organic hydroperoxides over a crystalline molecular sieve having the framework structure isomorphous with zeolite beta and containing Si and Ti, but essentially no framework Al.

In spite of the success of the above-mentioned titanium silicates, there is a continuing need to synthesize highly active, selective, stable, and versatile heterogeneous olefin epoxidation catalysts in order to improve productivity and facilitate downstream separation.

According to the invention, it has now been found that a novel titanium dealuminated MCM-22-type material, prepared by the impregnation of a dealuminated MCM-22 with $TiCl_4$, is a highly active olefin epoxidation catalyst which retains its catalytic activity after repeated uses. It is believed that this synthesis method isolates the titanium atoms inside the zeolite's supercages and surface pockets, thus preventing the formation of bulk $TiO_2$ particles.

SUMMARY OF THE INVENTION

In one aspect, the invention resides in a method of synthesizing an olefin epoxidation catalyst comprising the steps of:

(a) treating a porous crystalline aluminosilicate material having an X-ray diffraction pattern including d-spacing maxima at 12.4±0.25, 6.9±0.15, 3.57±0.07 and 3.42±0.07 Angstrom with a dealuminating agent under conditions effective to remove framework aluminum from said material and produce a dealuminated product; and then (b) treating the dealuminated product with a titanium-containing material under conditions effective to insert titanium into the dealuminated product and produce a titanium-containing, dealuminated catalyst composition.

Preferably, the porous crystalline aluminosilicate material is MCM-22.

Preferably, the dealuminating agent is silicon tetrachloride.

Preferably, the titanium-containing material is titanium tetrachloride.

In a further aspect, the invention resides in the use of the titanium-containing, dealuminated catalyst composition as an olefin epoxidation catalyst.

DETAILED DESCRIPTION OF THE INVENTION

The present invention relates to an olefin epoxidation catalyst which is synthesized from a porous crystalline aluminosilicate material having an X-ray diffraction pattern including d-spacing maxima at 12.4±0.25, 6.9±0.15, 3.57±0.07 and 3.42±0.07 Angstrom by treating the material with a dealuminating agent under conditions effective to remove framework aluminium from said material and produce a dealuminated product; and then treating the dealuminated product with a titanium-containing material under conditions effective to insert titanium into the dealuminated product.

The porous crystalline materials used in the present invention are characterized by having two independent pore systems, one of which is defined by two-dimensional, ten-ring, sinusoidal channels, and the other of which is defined, depending on the material involved, by twelve-ring supercages or surface pockets. It is believed that method of the invention results in titanium atoms being inserted into the supercages and/or surface pockets, rather than into the sinusoidal channels, of the crystalline material.

Suitable porous crystalline aluminosilicate materials are MCM-22 (described in U.S. Pat. No. 4,954,325), PSH-3 (described in U.S. Pat. No. 4,439,409), SSZ-25 (described in U.S. Pat. No. 4,826,667), MCM-36 (described in U.S. Pat. No. 5,250,277), MCM-49 (described in U.S. Pat. No. 5,236,575) and MCM-56 (described in U.S. Pat. No. 5,362,697), with MCM-22 being particularly preferred.

The porous crystalline aluminosilicate material is initially treated with a with a dealuminating agent under conditions effective to remove framework aluminium from said material. Post-synthesis dealumination of zeolites is well known in the art and is described in, for example, U.S. Pat. No. 4,954,325. Suitable dealuminating agents include mineral acids, chelating agents, steam and compounds capable of isomorphous substitution for the aluminum in the framework of the aluminosilicate material. The latter are preferred with suitable compounds being silicon tetrachloride and silicon hexafluoride, such that the aluminum in the framework of the aluminosilicate material is replaced with silicon.

A preferred dealumination treatment involves contacting the aluminosilicate material with silicon tetrachloride in the vapor phase at a temperature of 100° C. to 1000° C., preferably 200° C. to 800° C., and most preferably 350° C. to 550° C. for a time of 0.01 to 100 hours, preferably 0.1 to 24 hours. The dealumination treatment is conveniently performed in a transport reactor, which is essentially a closed loop of quartz tubing that allows for a circulating convection current of the inorganic halide to be established over the heated aluminosilicate material. Volatile byproducts of the framework substitution reaction, e.g., $AlCl_3$, are transported away from the reaction zone and accumulate on the colder surfaces. The same dealumination step could also be performed with other reactors, e.g. a fluidized-bed reactor, where the volatile $AlCl_3$ is removed from the reaction zone by a carrier gas such as He, Ar, $N_2$, or other gas inert to the dealumination reaction.

The dealuminated product is then contacted with a titanium-containing material under conditions effective to insert titanium into the dealuminated product and produce a titanium-containing, dealuminated catalyst composition. For example, the dealuminated product may be contacted with a volatile titanium compound, such as $TiCl_4$, at a temperature of −20° C. to 1000° C., preferably 0° C. to 800° C., most preferably 20° C. to 550° C., for a time for a time of 0.01 to 100 hours. Again a transport reactor is conveniently used to perform vapor-phase titanium treatment. Similar to the dealumination step, other reactors such as a fluidized-bed reactor are also suitable for the vapor phase titanium treatment. Alternatively, the titanium treatment can be effected by contacting the dealuminated product with a liquid phase source of titanium, for example $(NH_4)_2TiF_6$ or $TiF_4$ dissolved in a suitable solvent. Methods of post-synthesis titanium incorporation into zeolites is well known in the art and are described in, for example, U.S. Pat. No. 4,576,805.

The resultant titanium-containing, dealuminated composition can be used as a catalyst in the epoxidation of olefins either directly or after being combined with a matrix or binder, preferably a non-acidic binder, such as silica.

The process of the invention is especially useful for the epoxidation of $C_2$–$C_{20}$ olefins, and more preferably $C_2$–$C_{16}$ monoolefins. Examples of suitable olefins include, but are not limited to, ethylene, propylene, 1-butene, 2-butene, isobutylene, 1-pentene, 2-pentene, cyclopentene, 1-hexene, cyclohexene, 1-heptene, 1-octene, 1-decene, 1-dodecene, 1-tetradecene, and 1-hexadecene. The oxidizing agent employed is preferably hydrogen peroxide or an organic hydroperoxide, such as t-butyl hydroperoxide, t-amyl hydroperoxide, cumene hydroperoxide, ethylbenzene hydroperoxide or cyclohexyl hydroperoxide. The ratio of olefin to oxidizing agent is not critical but generally is in the range 100:1 to 1:100, more preferably 20:1 to 1:20.

The epoxidation process of the invention is effected by contacting the olefin and the oxidizing agent with the titanium-containing, dealuminated catalyst composition described above in the liquid phase at a temperature of 0 to 150° C., preferably 20 to 120° C., and a pressure of atmospheric to 1000 psig, preferably atmospheric to 400 psig. To effect the epoxidation process, the catalyst may be contained in a stationary or fluidized bed, and the contacting operation may take place continuously or batch-wise. If the contacting takes place continuously, the LHSV based on olefin is within the range of 0.1 to 100 $hr^{-1}$, preferably 1 to 50 $hr^{-1}$. If the contacting takes place batch-wise, the residence time is within the range of 1 to 600 min, preferably 1 to 180 min. The olefin and peroxide can be dissolved in a solvent such as benzene, toluene, cumene or other organic solvents inert to the oxidation reaction.

EXAMPLE 1

0.221 g of MCM-22 crystals were dealuminated at 500° C. with $SiCl_4$ for 4.5 hours using a transport reactor. The dealuminated solid was dried under vacuum at 450° C. for 1 hour, and impregnated with $TiCl_4$ vapor at 100° C., using a transport reactor, for 24 hours. After impregnation, the solid sample (abbreviated as Ti—De—Al-MCM-22 hereafter) was exposed to water vapor at 20° C. for 2 hours and dried under vacuum at 125° C. for 2 hours.

EXAMPLE 2

To a 250-ml round-bottom flask fitted with a condenser, a magnetic stirrer and a dropping funnel were added 0.212 g of the Ti—De—Al-MCM-22 solid from Example 1 and 100 g cyclohexene. The reaction flask was maintained at 80° C. and 50 g of technical grade cumene hydroperoxide (80.8% CHP, 7.7% cumene, 6.9% 2-phenyl-2-propanol, 2.1% acetophenone) was added drop-wise at an approximate rate of 3–4 g/min. Following addition of the CHP solution, small samples (~0.2 ml) of the reactant solution were withdrawn at regular intervals, filtered, and analyzed by GC.

Table 1 shows the composition (wt. %) of the reactant solution at 90 minutes after the addition of the CHP. Cyclohexene conversion was 50.1% and cyclohexene oxide selectivity was 90.7%. These data indicate that the Ti—De—Al-MCM-22 solid is an active cyclohexene epoxidation catalyst with superior cyclohexene oxide selectivity than the titanium-containing beta catalysts of U.S. Pat. Nos. 5,374,747 and 5,621,122 (which are disclosed as having cyclohexene oxide selectivities of 58–75%).

EXAMPLE 3

The solid catalyst from the Example 2 was recovered by filtration and calcined at 500° C. for 10 hours. Elemental analysis showed the calcined sample contained 0.89% Ti, 0.11% Al, and 37.27% Si.

0.115 g of the above-recovered solid was used as the catalyst for a repeat of the cyclohexene epoxidation procedure of Example 2.

Table 1 shows the composition (wt. %) of the reactant solution at 90 minutes after the addition of the CHP. Cyclohexene conversion was 38.0%, cyclohexene oxide selectivity was 64.4%. These data indicate that the $TiCl_4$-impregnated dealuminated MCM-22 material was still an active olefin epoxidation catalyst after a repeated use. Comparing the cyclohexene conversion level and the catalyst amount in this repeated experiment with those in the Example 2 shows that the recovered catalyst was virtually as active as the original catalyst.

Comparative Example 4

A solution of 2.3 g titanium oxysulfate-sulfuric acid complex hydrate ($TiSO_4 \cdot xH_2SO_4 \cdot xH_2O$, x~1) in 10 g of deionized water was added dropwise to 22.5 g Ultrasil silica. The impregnated material was dried overnight at 85° C. and then calcined in air at 500° C. for 3 h. The resultant $TiO_2$—$SiO_2$ solid (0.996 g, 2.01% Ti) was investigated as a cyclohexene epoxidation catalyst using procedure of Example 2.

Table 1 shows the composition (wt. %) of the reactant solution at 90 minutes after the addition of the CHP. Cyclohexene conversion was 50.7%, cyclohexene oxide selectivity was 81.2%.

Comparing the cyclohexene conversion level and the catalyst amount in this Example with those in the Example 2 shows that in order to achieve the same cyclohexene conversion level at the same reaction time, five times more of the $TiO_2$—$SiO_2$ catalyst (0.996 g) was needed than the Ti—De—Al-MCM-22 (0.212 g). This result demonstrates that Ti—De—Al-MCM-22 is a more active cyclohexene epoxidation catalyst than $TiO_2$—$SiO_2$ prepared by impregnation.

Comparative Example 5

For comparison, dealuminated MCM-22 (0.187 g) that had not been subjected to $TiCl_4$ impregnation was investigated for its catalytic activity towards cyclohexene epoxidation. The MCM-22 was dealuminated at 500° C. with $SiCl_4$ for 2.5 hours in a transport reactor. The epoxidation procedure of Example 2 was followed.

Table 1 shows the composition (wt. %) of the reactant solution at 78 minutes after the addition of the CHP. Cyclohexene conversion was 2.2%, cyclohexene oxide selectivity was 44.0%. These data indicate that without the $TiCl_4$ impregnation, dealuminated MCM-22 has negligible catalytic activity for cyclohexene epoxidation.

Comparative Example 6

For comparison, MCM-22 (0.200 g) that had not been subjected to dealumination or $TiCl_4$ impregnation was investigated for its catalytic activity towards cyclohexene epoxidation. The same procedure as that of the Example 2 was followed.

Table 1 shows the composition (wt. %) of the reactant solution at 90 minutes after the addition of the CHP. As the data in Table 1 show, MCM-22 that had not been subjected to dealumination or $TiCl_4$ impregnation was totally inactive for cyclohexene epoxidation.

TABLE 1

| Example | Feed | 2 | 3 | 4 | 5 | 6 |
|---|---|---|---|---|---|---|
| Catalyst | | Ti-DeAl-MCM-22 | Ti-DeAl-MCM-22 | Ti/SiO$_2$ | DeAl-MCM-22 | MCM-22 |
| Weight (g) | | 0.212 | 0.115 | 0.996 | 0.187 | 0.2002 |
| Ti, wt. % | | N/A | 0.89 | 2.01 | N/A | N/A |
| Al, wt % | | N/A | 0.11 | 0.062 | N/A | N/A |
| Temperature (° C.) | | 85.0 | 80.0 | 80.0 | 80.0 | 80.0 |
| Time, min | | 90.0 | 90.0 | 90.0 | 78.0 | 90.0 |
| Product Composition (wt. %) | | | | | | |
| Acetone | | 0.08 | 0.04 | 0.06 | 0.08 | 9.03 |
| Cyclohexene | 66.67 | 59.38 | 61.14 | 59.29 | 63.44 | 67.36 |
| Cyclohexene Oxide | | 7.89 | 4.25 | 7.16 | 0.18 | 0.00 |
| p-Benzoquinone | | 0.16 | 0.21 | 0.15 | 0.21 | 0.47 |
| Cumene | 2.56 | 2.62 | 2.60 | 2.62 | 2.66 | 2.72 |
| Phenol | 0.09 | 0.05 | 0.04 | 0.06 | 0.08 | 14.67 |
| alpha-MeStyrene | 0.07 | 0.11 | 0.08 | 0.12 | 0.10 | 0.38 |
| Acetophenone | 0.69 | 0.67 | 0.68 | 0.69 | 0.79 | 2.84 |
| 2-Ph-2-Propanol | 2.36 | 13.94 | 8.83 | 13.19 | 2.87 | 0.29 |
| o-OH-Acetophenone | | 0.03 | 0.03 | 0.04 | 0.04 | 0.00 |
| CumeneHP | 26.93 | 14.64 | 21.52 | 16.00 | 28.58 | 1.31 |
| Others | 0.63 | 0.43 | 0.58 | 0.62 | 0.97 | 0.93 |
| CHP Conversion | | 45.7% | 20.1% | 40.6% | 6.7% | 95.1% |
| Cyclo-C$_6^=$ Conversion | | 50.1% | 38.0% | 50.7% | 2.2% | −3.2% |
| Cyclo-C$_6^=$ Oxide Selectivity | | 90.7% | 64.4% | 81.2% | 44.0% | 0.00 |

What we claim is:

1. A method of synthesizing an olefin epoxidation catalyst comprising the steps of:
    (a) treating a porous crystalline aluminosilicate material having an X-ray diffraction pattern including d-spacing maxima at 12.4±0.25, 6.9±0.15, 3.57±0.07 and 3.42±0.07 Angstrom with a dealuminating agent to remove framework aluminium from said material and produce a dealuminated product; and then
    (b) treating the dealuminated product with a titanium-containing material to insert titanium into the dealuminated product and produce a titanium-containing, dealuminated catalyst composition.

2. The method of claim 1 wherein the porous crystalline aluminosilicate material is MCM-22.

3. The method of claim 1 wherein the dealuminating agent is effective to replace framework aluminium in said crystalline aluminosilicate material with silicon.

4. The method of claim 3 wherein the dealuminating agent is silicon tetrachloride.

5. The method of claim 1 wherein the titanium-containing material is titanium tetrachloride.

6. A process for epoxidation of an olefin comprising the step of contacting said olefin with an oxidizing agent selected from hydrogen peroxide or an organic hydroperoxide in the presence of a titanium-containing, dealuminated catalyst composition produced by a method comprising the steps of:

(a) treating a porous crystalline aluminosilicate material having an X-ray diffraction pattern including d-spacing maxima at 12.4±0.25, 6.9±0.15, 3.57±0.07 and 3.42±0.07 Angstrom with a dealuminating agent to remove framework aluminium from said material and produce a dealuminated product; and then (b) treating the dealuminated product with a titanium-containing material to insert titanium into the dealuminated product and produce said titanium-containing, dealuminated catalyst composition.

7. The process of claim 6 wherein said contacting step is conducted at a temperature of 0 to 150° C. and a pressure of atmospheric to 1000 psig.

8. The process of claim 6 wherein said contacting step is conducted at a temperature of 20 to 120° C. and a pressure of atmospheric to 400 psig.

* * * * *